US012579714B2

(12) United States Patent
Fieselmann et al.

(10) Patent No.: US 12,579,714 B2

(45) Date of Patent: Mar. 17, 2026

(54) COMPUTER-IMPLEMENTED METHOD FOR PROVIDING A DE-IDENTIFIED MEDICAL IMAGE

(71) Applicant: Siemens Healthineers AG, Forchheim (DE)

(72) Inventors: Andreas Fieselmann, Erlangen (DE); Steffen Kappler, Effeltrich (DE); Christian Huemmer, Lichtenfels (DE); Ramyar Biniazan, Nuremberg (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 272 days.

(21) Appl. No.: 18/476,838

(22) Filed: Sep. 28, 2023

(65) Prior Publication Data

US 2024/0127516 A1 Apr. 18, 2024

(30) Foreign Application Priority Data

Sep. 30, 2022 (EP) .................................... 22199068

(51) Int. Cl.
| | |
|---|---|
| *G06T 11/60* | (2006.01) |
| *G06V 10/74* | (2022.01) |

(Continued)

(52) U.S. Cl.
CPC ........... *G06T 11/60* (2013.01); *G06V 10/761* (2022.01); *G06V 10/774* (2022.01); *G16H 30/40* (2018.01);

(Continued)

(58) Field of Classification Search
CPC ................................. G06T 11/60; G16H 30/40
See application file for complete search history.

(56) References Cited

U.S. PATENT DOCUMENTS

| | | | |
|---|---|---|---|
| 2021/0350176 A1* | 11/2021 | Klaiman | ............... G06F 18/214 |
| 2022/0237788 A1* | 7/2022 | Shaul | ..................... G16H 50/70 |

(Continued)

OTHER PUBLICATIONS

Ko D.H.et al.: "Structural Image De-Identification for Privacy-Preserving Deep Learning", IEEE Access, vol. 8, pp. 119848-119862,2020.

(Continued)

*Primary Examiner* — Edward Park

(74) *Attorney, Agent, or Firm* — Harness, Dickey & Pierce, P.L.C.

(57) ABSTRACT

A computer-implemented method, comprising: receiving input data including a medical image and an in-image annotation; applying a first function to the input data to determine a relevance value of pixels in the image and a relevance map; applying a second function to the medical image to generate a de-identified medical image; applying a trained function to the medical image and the de-identified medical image to determine a first property in the medical image and a second property in the de-identified medical image; applying a comparison function to the first property and the second property to determine a similarity value, wherein in response to the similarity value being below a similarity threshold, the relevance map is adjusted and the applying of the second function, the applying of the trained function and the applying of the comparison function are repeated; and providing the de-identified medical image and the in-image annotation.

18 Claims, 5 Drawing Sheets

(51) Int. Cl.
    *G06V 10/774*     (2022.01)
    *G16H 30/40*     (2018.01)

(52) U.S. Cl.
    CPC ...... *G06T 2210/41* (2013.01); *G06V 2201/03*
                        (2022.01)

(56)               References Cited

U.S. PATENT DOCUMENTS

2024/0127516 A1*   4/2024   Fieselmann ............ G16H 30/40
2025/0316061 A1*  10/2025   Kara ........................ G06N 3/08

OTHER PUBLICATIONS

Diaz et al.: Data preparation for artificial intelligence in medical imaging: A comprehensive guide to open-access platforms and tools, Physica Medica, vol. 83, pp. 25-37, 2021.
Cynthia Dwork; Aaron Roth; "The Algorithmic Foundations of Differential Privacy"; Foundations and Trends in Theoretical Computer Science vol. 9, Nos. 3-4 (2014) 211-407;2014; DOI: 10.1561/0400000042; 2014.
Van Der Goten, Lennart Alexander et al: "Conditional De-Identification of MRI Scans Conditional De-Identification of 3D Magnetic Resonance Images", Oct. 18, 2021 (Oct. 18, 2021), XP093020521, Retrieved from the Internet: URL:https://arxiv.org/abs/2110.09927 [retrieved on Feb. 3, 2023].
Kaissis G.A. et al.:"Secure, privacy-preserving and federated machine learning in medical imaging", Nature Machine Intelligence, vol. 2, pp. 305-311, 2021.

\* cited by examiner

IIA

DII log(1+abs(DII-I))

FIG 5

COMPUTER-IMPLEMENTED METHOD FOR PROVIDING A DE-IDENTIFIED MEDICAL IMAGE

CROSS-REFERENCE TO RELATED APPLICATION(S)

The present application claims priority under 35 U.S.C. § 119 to European Patent Application No. 22199068.2, filed Sep. 30, 2022, the entire contents of which is incorporated herein by reference.

FIELD

One or more example embodiments of the present invention relate to a computer-implemented method for providing a de-identified medical image, wherein the de-identified medical image is modified in less diagnostically relevant regions.

BACKGROUND

An X-ray imaging system, e.g. a radiography system or a fluoroscopy system, comprises an X-ray source and an X-ray detector. The examination object, in particular a patient, is arranged between the X-ray source and the X-ray detector so that an X-ray image of an examination region can be acquired. Machine learning, in particular deep learning (DL), has proven to provide benefits for many medical image analytics applications. As an example, DL models can detect certain pathologies in chest x-ray images and DL models have also shown benefit for detection of anatomical landmarks in orthopedic x-ray images for quantification of joint misalignment.

To train DL models, one requires a high quantity of high-quality images and annotations sampled from a realistic and diverse patient population, ideally from different locations.

Medical images are usually considered to be sensitive data, as it may be possible to track back a certain image to an individual patient. Data minimization techniques can remove personal meta information (such as patient name). However, the pixel data itself could also be used to track back an image to an individual patient. As an example, a unique hash value could be computed from the pixel data from a digital imaging and communications in medicine (DICOM) file. If one knew where the image had been acquired and had access to the images of the picture archiving and communication system (PACS) one could search for the image in the PACS using hash values computed from the images in the PACS.

Due to this risk often the transfer of the image data from a hospital to a third party (e. g. a company developing software based on DL models) is often denied. However, as a third party, it would be beneficial to have access to the pixel data to optimize DL model training (e. g. analysis of cases where the prediction fails; or to allow for more effective training of a DL model based on a central database of images).

SUMMARY

An underlying problem for one or more example embodiments of the present invention is that medical images (such as x-ray images) are needed for DL training, and it is particular useful when they are accessible from a central data base but often transfer of such images from a hospital, for example, to the database is denied due to concerns that by technical mechanisms and/or means the identity of the patient could be revealed.

One or more example embodiments of the present invention provide a technical solution that effectively prevents patient re-identification based on the pixel data while maintaining the usefulness of the medical image for DL model training by a third party.

De-identification of meta data from DICOM images (information in the DICOM header) is common routine and not the scope of this invention. Manipulation of the pixel data in order to remove protected health information (PHI) and personal identifiable information (PII) is known, especially for removal of text visible in the medical image (burned in PHI/PII data annotations) e. g. in ultrasound images, removal of facial features. However, this manipulation of pixel data is optimized for a human interpretation of the image, and it does not check if the manipulations have an effect on the training of a DL model based on the image.

The following publications disclose methods for de-identification of medical images:

Kaissis et al. (2020), "Secure, privacy-preserving and federated machine learning in medical imaging", Nature Machine Intelligence, vol. 2, pp. 305-311, https://doi.org/10.1038/s42256-020-0186-1

Ko et al. (2020), "Structural Image De-Identification for Privacy-Preserving Deep Learning", IEEE Access, vol. 8, pp. 119848-119862, http://doi.org/10.1109/ACCESS.2020.3005911

Roth and Dwork (2014), "The algorithmic foundations of differential privacy", Found. Trends Theoretical Comp. Sci., vol. 9, pp. 211-407, https://doi.org/10.1561/0400000042

Privacy-preserving deep learning (PPDL) is a research field addressing DL training on data without revealing the original data. Differential privacy (DP) was introduced by Roth and Dwork (2014) and aims at retaining the global statistical distribution of a dataset while reducing individually recognizable information (Kaissis (2020)). DP methods perturbate the whole image (e. g. by adding noise) and do not distinguish between areas in the image that are of higher or lesser relevance for the deep learning task.

Ko et al. (2020) have presented a method for PPDL that uses a structural image de-identification approach. They transformed the whole image into a representation that is very different for the human eye compared to the original image. The image can still be used for DL training (e. g. object detection) and their experiments showed that similar accuracy can be reached without and with their PPDL method applied.

It is an object of one or more example embodiments of the present invention to provide a computer-implemented method for providing a de-identified medical image, a computer-implemented method for providing a trained function, a providing system, a computer program product, a computer-readable medium, a training system, and an X-ray system, which allow a non-homogenous de-identification of the medical image.

At least the above-mentioned object of one or more example embodiments of the present invention is solved by a computer-implemented method for providing a de-identified medical image according to claim 1, a computer-implemented method for providing a trained function according to claim 10, a providing system according to claim 11, a computer program product according to claim 12, a computer-readable medium according to claim 13, a training system according to claim 14, and an X-ray system according to claim 15.

In the following the solution according to embodiments of the present invention is described with respect to the claimed providing systems as well as with respect to the claimed methods. Features, advantages or alternative embodiments herein can be assigned to the other claimed objects and vice versa. In other words, claims for the providing systems can be improved with features described or claimed in the context of the methods. In this case, the functional features of the method are embodied by objective units of the providing system.

Furthermore, in the following the solution according to embodiments of the present invention is described with respect to methods and systems for providing a de-identified medical image as well as with respect to methods and systems for the training of the trained function. Features, advantages or alternative embodiments herein can be assigned to the other claimed objects and vice versa. In other words, claims for methods and systems for training of the trained function can be improved with features described or claimed in context of the methods and systems for providing a de-identified medical image, and vice versa.

In particular, the trained function of the methods and systems for providing a de-identified medical image can be adapted by the methods and systems for training of the trained function. Furthermore, the input data can comprise advantageous features and embodiments of the training input data, and vice versa. Furthermore, the output data can comprise advantageous features and embodiments of the output training data, and vice versa.

One or more example embodiments of the present invention relate to a computer-implemented method for providing a de-identified medical image, comprising:

Receiving input data, wherein the input data is a medical image and an in-image annotation based on the medical image, Applying a first function to the input data, wherein a relevance value of pixels in the medical image is determined based on the in-image annotation and thereof a relevance map is generated, Applying a second function to the medical image, and thereby generate a de-identified medical image based on the relevance map, Applying a trained function to the medical image and the de-identified medical image, and thereby determine a first property in the medical image and determine a second property in the de-identified medical image, Applying a comparison function to the first property and the second property, wherein the first property and the second property are compared to each other, and a similarity value is determined, in case the similarity value is below a similarity threshold, the relevance map is adjusted and the steps of applying the second function, applying the trained function and applying the comparison function are repeated, preferably until the similarity value is above a similarity threshold, Providing the de-identified medical image and the in-image annotation.

According to an aspect of embodiments of the present invention, applying the second function comprises modifying, blurring, adding noise or adding geometrically distortions in regions with pixels of lower relevance.

According to an aspect of embodiments of the present invention, the strength of modifying, blurring, adding noise or adding geometrically distortions depends on the relevance values.

According to an aspect of embodiments of the present invention, the relevance map comprises relevance value ranging from 0 to 1.

According to an aspect of embodiments of the present invention, the relevance value is determined based on a distance map which is based on the in-image annotations and pixels inside the in-image annotations.

According to an aspect of embodiments of the present invention, a second trained function is applied to the medical image, wherein additional non-relevant pixels are determined based on the information in the medical image.

According to an aspect of embodiments of the present invention, first property and/or the second property is determined by an object segmentation task, an object detection task, an image classification task, or a regression task.

According to an aspect of embodiments of the present invention, the similarity value is a Hausdorff distance, a difference of normalized probabilities or a difference of prediction results.

According to an aspect of embodiments of the present invention, the medical image is an X-ray image.

One or more example embodiments of the present invention further relate to a computer-implemented method for providing a trained function, comprising:

Receiving input training data, wherein the input training data comprises a medical image and/or a de-identified image, Receiving output training data, wherein the output training data is related to the input training data, wherein the output training data comprises an in-image annotation and/or a global annotation, Training a function based on the input training data and the output training data, Providing the trained function.

One or more example embodiments of the present invention further relate to a providing system comprising:

A first interface, configured for receiving input data, wherein the input data is a medical image and an in-image annotation based on the medical image, A first computation unit, configured for applying a first function to the input data, wherein a relevance value of pixels in the medical image is determined based on the in-image annotation and thereof a relevance map is generated, A second computation unit, configured for applying a second function to the medical image, and thereby generate a de-identified medical image based on the relevance map, A third computation unit, configured for applying a trained function to the medical image and the de-identified medical image, and thereby determine a first property in the medical image and determine a second property in the de-identified medical image, A fourth computation unit, configured for applying a comparison function to the first property and the second property, wherein the first property and the second property are compared to each other, and a similarity value is determined, in case the similarity value is below a similarity threshold, the relevance map is adjusted and the steps of applying the second function, applying the trained function and applying the comparison function are repeated,

A second interface, configured for providing the de-identified medical image and the in-image annotation.

One or more example embodiments of the present invention further relate to a computer program product comprising instructions which, when the program is executed by a providing system, cause the providing system to carry out the method according to embodiments of the present invention.

A computer-readable medium comprising instructions which, when executed by a providing system, cause the providing system to carry out the method according to embodiments of the present invention.

One or more example embodiments of the present invention further relate to a training system, comprising:

A first training interface, configured for receiving input training data, wherein the input training data comprises a medical image and/or a de-identified image, A second training interface, configured for receiving output training data, wherein the output training data is related to the input training data, wherein the output training data comprises an in-image annotation and/or a global annotation, A training computation unit, configured for training a function based on the input training data and the output training data, A third training interface, configured for providing the trained function.

One or more example embodiments of the present invention further relate to a medical imaging system comprising the providing system according to embodiments of the present invention.

In general, parameters of a trained function can be adapted via training. In particular, supervised training, semi-supervised training, unsupervised training, reinforcement learning and/or active learning can be used. Furthermore, representation learning (an alternative term is "feature learning") can be used. In particular, the parameters of the trained functions can be adapted iteratively by several steps of training.

In particular, a trained function can comprise a neural network, a support vector machine, a decision tree and/or a Bayesian network, and/or the trained function can be based on k-means clustering, Q-learning, genetic algorithms and/or association rules. In particular, a neural network can be a deep neural network, a convolutional neural network or a convolutional deep neural network. Furthermore, a neural network can be an adversarial network, a deep adversarial network and/or a generative adversarial network.

The problem underlying this invention is that pixel data in an image could be used to re-identify an individual patient, which prevents image transfer to a third party. The problem is solved by this invention by locally dependent modification of the pixel data while maintaining the overall usefulness of the medical image for DL model training confirmed by an internal check based on an existing DL model. Here, the main input data consists of the original image and an in-image annotation provided by a human for identifying an interesting area.

To illustrate one or more embodiments of the present invention by a practical example, an application from MSK x-ray imaging is chosen. Note however, that embodiments of the present invention can be applied to a variety of applications and is not limited to MSK X-ray imaging and can be applied for various medical images. Within the example, the medical image is a (knee) X-ray image.

A knee X-ray image is acquired in the hospital to make measurements of anatomical properties (length, angles).

The knee X-ray image is processed by a DL model to localize anatomical landmarks in a knee x-ray image relevant for the measurements.

The landmarks are shown to the doctor or user. If the results are not accepted by the doctor or user, they can be manually corrected. In this case the knee x-ray image and the doctor-corrected landmarks are valuable data for DL model re-training. With this data included into the training, the accuracy of the DL model could be improved in the future. Thus, transfer of this data to the third party that has developed the DL model would be beneficial.

Before the data (knee x-ray image, doctor-corrected annotation) is transferred to the third party, the data is processed by the method described in this invention to reduce the risk of re-identification based on the pixel data.

It is possible to re-train the DL model with locally aggregated data and only send back updated neural network weights to a central data base (Kaissis (2020)). However, having the (de-identified) image data with annotations transferred to a central data base has the advantage of a better overview and control of the DL model training process (e. g. analysis of failure cases).

As input data, a medical image (I) and an in-image annotation (IIA) are provided. Depending on the task, a global annotation (GA) might be available as well. For example, the medical image can be a chest x-ray (but can also be a 3D MRI volume or a 2D RGB video sequence of a patient), the in-image annotation can be a polygon annotation around a pneumothorax visible in the X-ray image and the global annotation can be a global classification (no/small/large pneumothorax or no/non-urgently/urgently to be treated pneumothorax etc.).

In step 1, a region of relevance (denoted as $\Omega$, the region of relevance can be either one connected component of consist of several unconnected components) is determined. $\Omega = Q(x,y)$ is a 2-D function dependent on the x/y coordinates in the image with values in the range [0, 1] where the extreme values indicate $\Omega = 0$: the pixel is considered to have low (or no) relevance for DL training $\Omega = 1$: the pixel is considered to have high relevance for DL training.

A relevance map can be determined. The relevance map can comprise relevance values $\Omega$ for each pixel.

There are different possible ways for determining $\Omega$, one of them is described in the following:

A distance map $D(x, y)$ is created based on the in-image annotation (IIA) and pixels inside IIA get assigned $\Omega = 1$, whereas the pixels outside of IIA get assigned $\Omega = f(D(x,y))$ where $f(r)$ is a function with property $f(0)=1$, $df/dr \leq 0$ and $f(rmax)=0$ where rmax is the maximum distance of a pixel from the border of the annotation at which it is still considered to be relevant for DL training.

In step 2, based on $\Omega$, especially based on the relevance map, the medical image I is de-identified. The de-identification operation can, for example, blur the image regions with a blurring strength based on $\Omega$ ($\Omega = 1$: no blurring, $\Omega = 0$: strongest blurring). Likewise, noise could be added based on $\Omega$ or the medical image could be geometrically distorted based on $\Omega$.

The aim is not to modify the image regions that are considered to have high relevance for DL training but to modify image regions which are considered to have low (or no) relevance for DL training to minimize the risk of patient re-identification.

Optionally, a separate DL model, also known as second trained function, could detect regions in the medical image (I) that are likely to contain PII (e. g. head region). These regions could also be de-identified (e. g. pixel values set to zero), independently of the $\Omega(x,y,)$ values in this region. The output of this step is a so-called de-identified image (DII). The term "de-identified image" should be interpreted in a way that the chances of re-identification of a patient based on this image are much lower compared to when the original image would be used.

In step 3, an existing and trained DL model is used to infer a first property from the image I and separately a second property also from the de-identified image DII. One would expect a very similar result for the first and second property. Note that the DL model could be updated regularly by the third party developing the DL model or by local retraining (see step 5). The property is task-specific and could be an object segmentation or object detection task (e. g. localizing a rib fracture), an image classification task (e. g. probability of a disease present in the image, probability of being from the same distribution as an already existing de-identified dataset) or a regression task (e. g. estimation of continuous bone ossification grade).

In step 4, a similarity check is made based on the two inference results, the first property and the second property. A task-specific metric (scalar value), also called similarity value, is calculated which could be Hausdorff distance (for a segmentation task), difference of normalized probabilities (for a classification task), difference of prediction results (for a regression task).

If the check passes, i. e. the comparison shows that the two inference results are very similar (similarity can be defined by the scalar value being above or below a certain threshold), then the conclusion is that applying the de-identification (step 2) to the image does not modify the inference result and—most likely—would not modify the DL training process either. In this case the de-identified image (DII) can be further used in steps 5 and 6, As a variant, in order to minimize the region of pixel data that is not changed (and therefore further decrease the risk of patient re-identification) the region of relevance (Q) could be decreased, e. g. rmax could be decreased by a certain factor, and steps 2 to 4 are repeated.

If the check fails, i. e. the comparison shows that the two inference results are not very similar, then a feedback loop takes place, and the region of relevance (Q) is adjusted in step 1. For example, rmax can be increased by a certain factor. The steps 2 and 3 are executed again and the check in step 4 is repeated.

Optionally, in step 5, a local re-training of the DL model introduced in step 3 can be made. To enable local re-training, all medical images (I) and de-identified images (DII) from the institution collected over time are stored locally. Additionally, depending on the type of inference task for each image the ground truth for the DL model should be stored. In case of a segmentation or detection task, the ground truth can be the IIA; in case of a classification or regression task the ground truth can be the GA. The local re-training can be triggered once a certain number of new medical images (I) has been collected. One can use either both of these pairs or only one of them, I and annotations (IIA and/or GA)

DII and annotations (IIA and/or GA)

for retraining.

In step 6, the de-identified image (DII), the in-image annotation (IIA) and, if available, the global annotation (GA) are provided and they can be transferred to e.g. a third party.

An advantage of embodiments of the present invention is an integrated check based on an existing DL model to evaluate, if the de-identified medical image (DII) that is later transferred to the third party is equivalent in terms of DL model inference (and indirectly DL model training) compared to the original medical image (I). A reduced risk of patient re-identification while maintaining high data quality for DL model training can be achieved. The ROI size where pixel data is not modified is determined individually for each image. Based on the check result (step 4) the region of relevance can be adjusted if needed. One or more embodiments of the present invention combine the advantages of local retraining (step 5) to improve local performance of the DL model with the advantage to transfer data for better DL model analysis and training to a third party (step 6).

Compared to an approach of simply cropping a region of interest (ROI) with the interesting pixel data (e. g. where there is a lesion), the method according to embodiments of the present invention make it possible to provide more spatial context information to the DL model training. A small ROI could miss information outside the ROI that contains anatomical relevance. By including a larger spatial region (where the pixel data is modified outside of the core region) that DL model can learn more anatomical context information. The size of the ROI is adapted in which the pixel data is not modified to the image (by adjustment of Q when the check in step 4 fails). This can be advantageous as a fixed ROI size is usually a trade-off between keep sufficient data and not to keep too much data.

Compared to published PPDL methods a modification is not applied to all pixel data. By using the in-image annotation (IIA) the modification is guided and applied in certain regions only. This approach does not modify pixel data which are highly relevant for DL model training. Keeping this pixel data in its original way can make subsequent steps in DL model training (e. g. data augmentation) more effective. As further advantage, our invention is independent of the DL model architecture and the task (segmentation, as long as in-image annotations are available.

BRIEF DESCRIPTION OF THE DRAWINGS

Examples of embodiments of the present invention are explained in more detail below with regard to the drawings.

FIG. 2 an example of an result provided by the method according to embodiments of the present invention;

FIG. 5 a schematic representation of an X-ray system.

DETAILED DESCRIPTION

Figure 1:
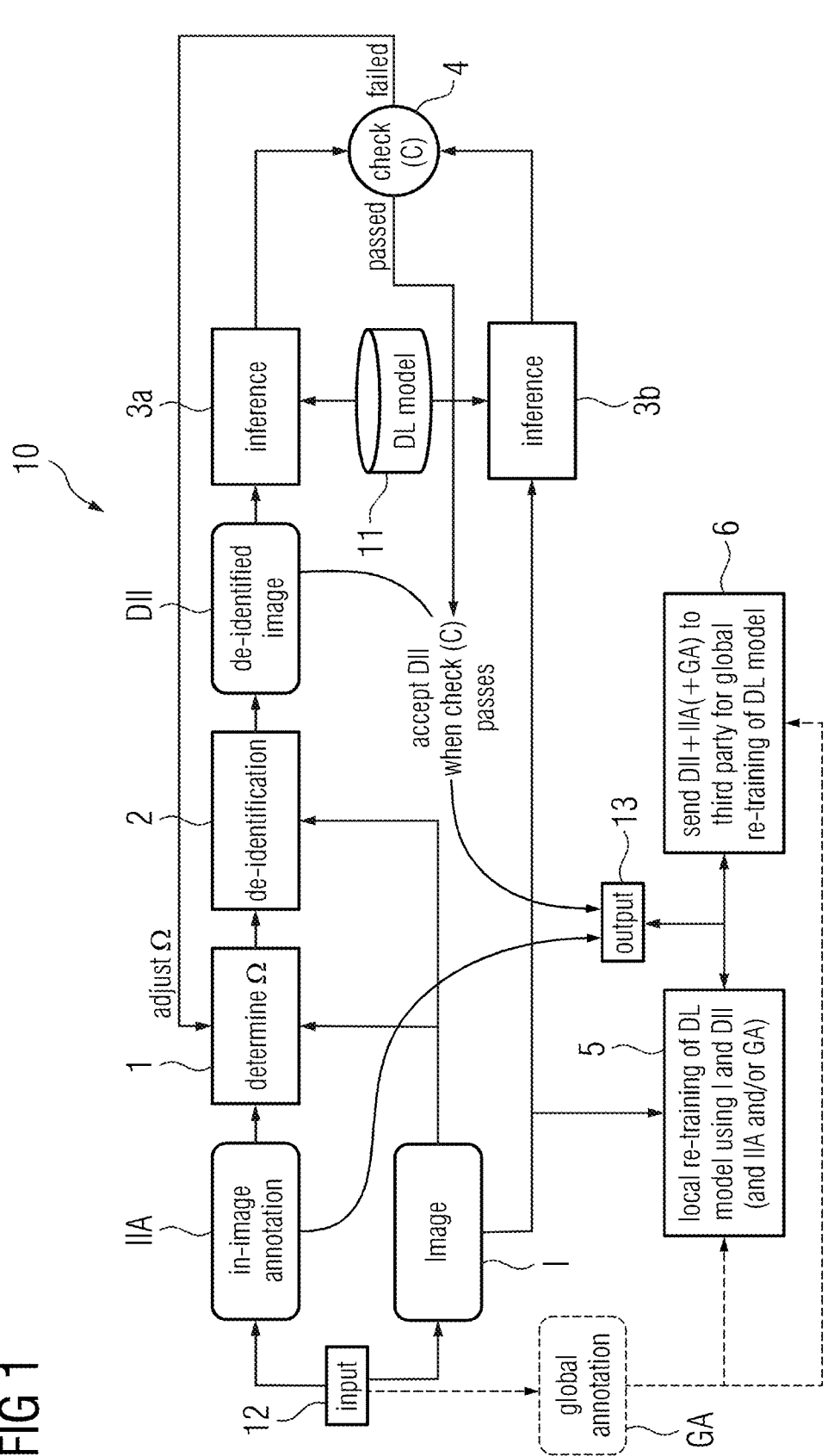
FIG. 1 a schematic representation of the method for providing a de-identified medical image.

FIG. 1 displays a computer-implemented method 10 for providing a de-identified medical image DII according to embodiments of the present invention. The method 10 comprises the following steps, preferably in the following order:

Receiving 12 input data, wherein the input data is a medical image I and an in-image annotation IIA based on the medical image, Applying 1 a first function to the input data, wherein a relevance value of pixels in the medical image is determined based on the in-image annotation and thereof a relevance map is generated, Applying 2 a second function to the medical image, and thereby generate a de-identified medical image DII based on the relevance map, Applying 3*a*, 3*b* a trained function 11 to the medical image and the de-identified medical image, and thereby determine a first property in the medical image and determine a second property in the de-identified medical image, Applying 4 a comparison function to the first property and the second property, wherein the first property and the second property are compared to each other and a similarity value is determined, in case the similarity value is below a similarity threshold, the relevance map is adjusted and the steps of applying the second function, applying the trained function and applying the comparison function are repeated, Providing 13 the de-identified medical image and the in-image annotation.

The de-identified medical image DII is accepted when the check or the comparison step is passed. The provided data can be supplied to a local re-training 5 of DL model (trained function 11) using the medical image I and the de-identified medical image DII. In addition, also the in-image annotation IIA and/or the global annotation GA can be supplied to the re-training 5. The provided data can be send 6 to another unit, e.g. of a third party, for global re-training of the DL model (trained function 11). The de-identified medical image DII, the in-image annotation IIA, and if available or necessary, the global annotation GA is sent to another unit.

Figure 2:
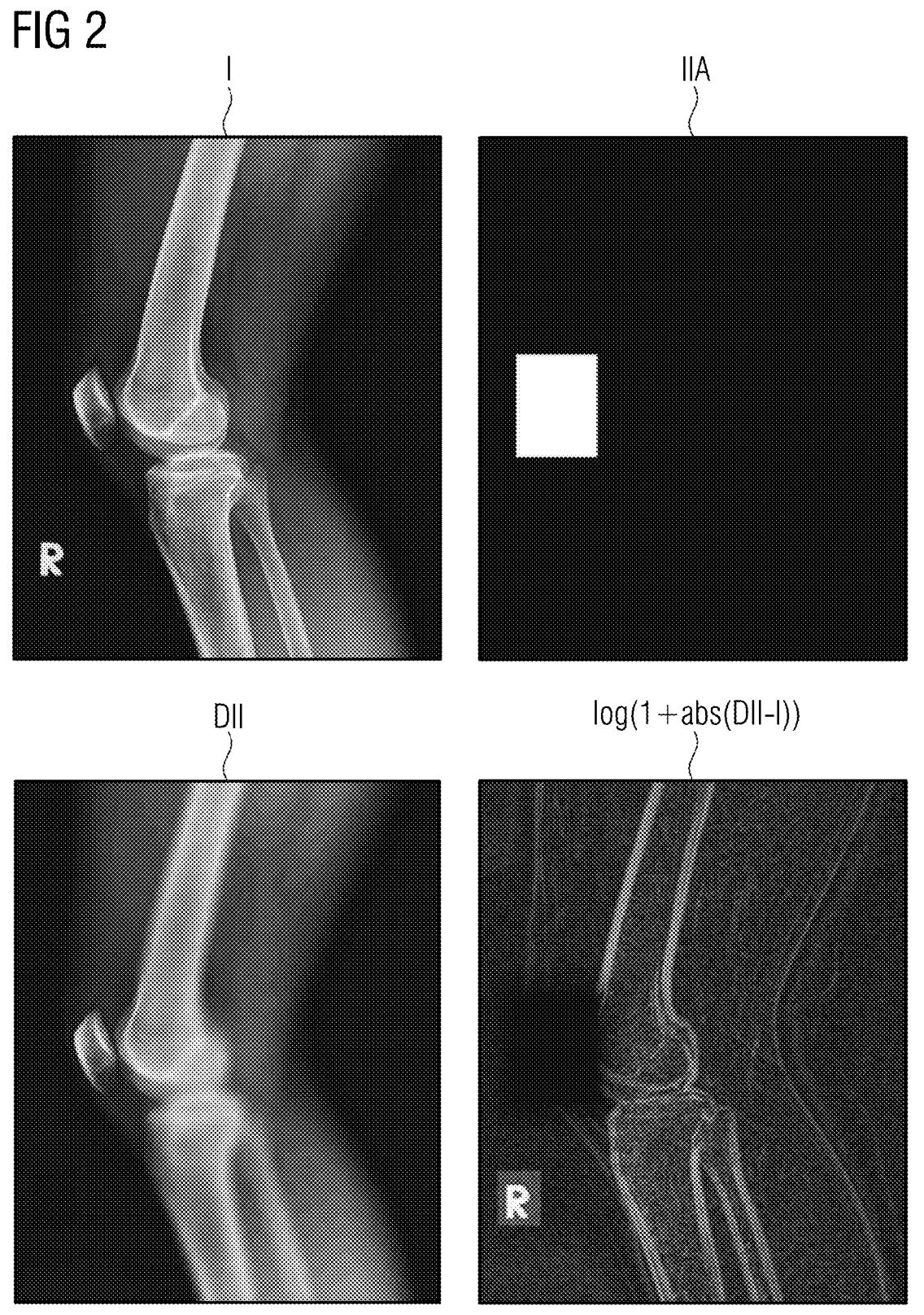

FIG. 2 displays an example for the applied method. In this example, a de-identified image (DII) from a knee x-ray image (I) is created. The ML model task for this example is to find certain anatomical landmarks at the patella on a knee x-ray (e. g. apex of the patella). If landmarks detection has failed (cf. step 3) then the doctor can correct them. Either the doctor can highlight the region of interest (patella) or the region of interest can be automatically determined based on the corrected landmarks (e.g. bounding box around all relevant landmarks).

In this example, based on the x-ray image (I) and the in-image annotation (IIA), the de-identified image (DII) is created by a distance map $D(x,y)$ is computed based on IIA, the region of relevance $\Omega(x,y)$ is computed as $\Omega(x,y)= 1-min(D(x,y)/rmax, 1)$, the de-identified image $DII(x,y)$ is computed as $DII(x,y)=\Omega(x,y)*I(x,y)+(1-(x,y))*Iproc$.

The image Iproc is a processed version of I in which the contrast (bit depth) is reduced, blurring is applied, and pixel noise is added.

The in-image annotation (IIA) is given as bounding box. The bottom right image shows a difference image between DII and I. Please note that the pixel values in the patella region are unchanged whereas other pixel values have undergone spatial filtering a contrast reduction operation and noise has been added. The "R" marked as additionally be removed as example that certain areas in the image can also be completely removed.

Figure 3:
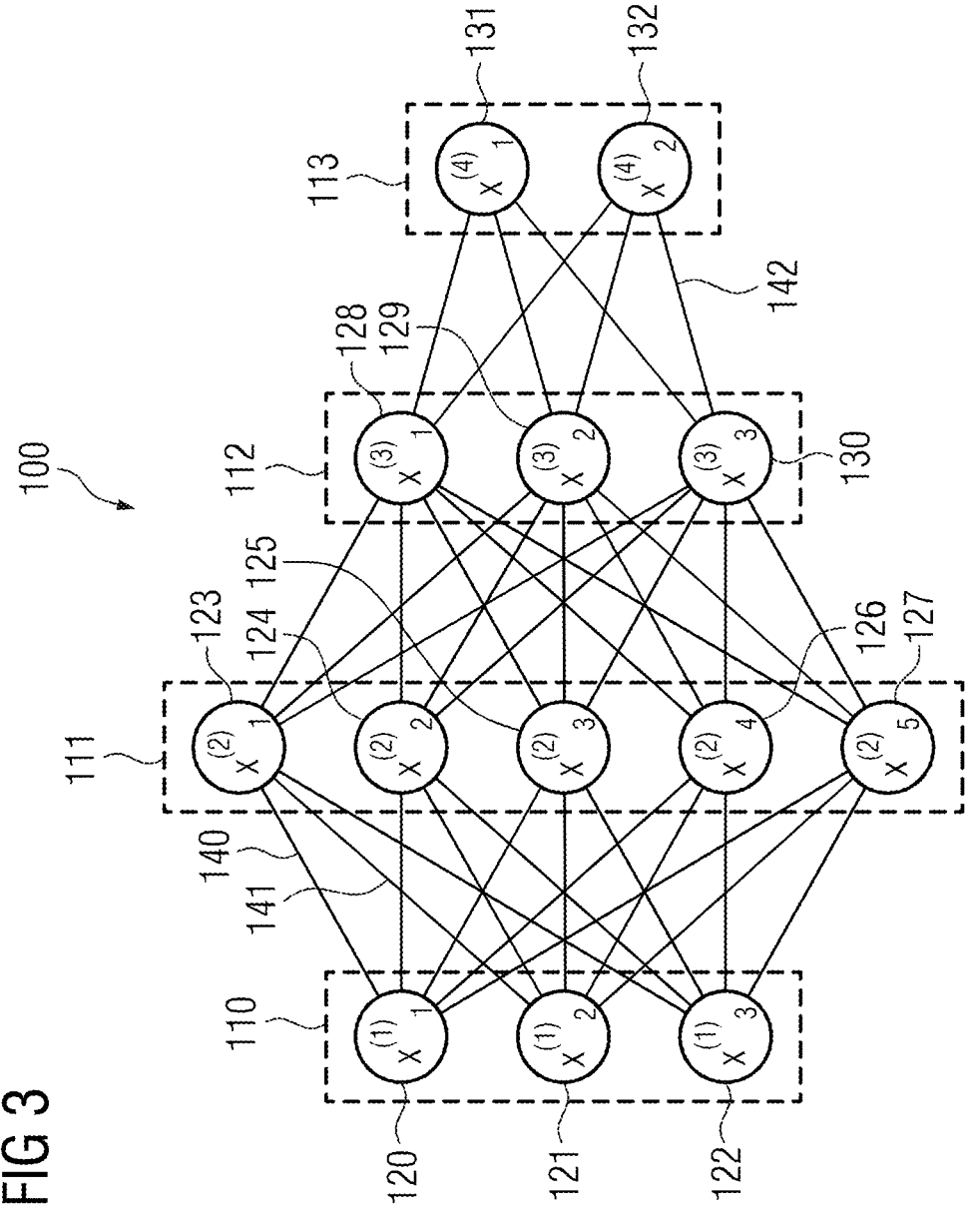
FIG. 3 a schematic representation of a neural network according to embodiments of the present invention.

FIG. 3 displays an embodiment of an artificial neural network 100. Alternative terms for "artificial neural network" are "neural network", "artificial neural net" or "neural net".

The artificial neural network 100 comprises nodes 120, . . . , 132 and edges 140, . . . , 142, wherein each edge 140, . . . , 142 is a directed connection from a first node

120, . . . , 132 to a second node 120, . . . , 132. In general, the first node 120, . . . , 132 and the second node 120, . . . , 132 are different nodes 120, . . . , 132, it is also possible that the first node 120, . . . , 132 and the second node 120, . . . , 132 are identical. For example, in FIG. 1 the edge 140 is a directed connection from the node 120 to the node 123, and the edge 142 is a directed connection from the node 130 to the node 132. An edge 140, . . . , 142 from a first node 120, . . . , 132 to a second node 120, . . . , 132 is also denoted as "ingoing edge" for the second node 120, . . . , 132 and as "outgoing edge" for the first node 120, . . . , 132.

In this embodiment, the nodes 120, . . . , 132 of the artificial neural network 100 can be arranged in layers 110, . . . , 113, wherein the layers can comprise an intrinsic order introduced by the edges 140, . . . , 142 between the nodes 120, . . . , 132. In particular, edges 140, . . . , 142 can exist only between neighboring layers of nodes. In the displayed embodiment, there is an input layer 110 comprising only nodes 120, . . . , 122 without an incoming edge, an output layer 113 comprising only nodes 131, 132 without outgoing edges, and hidden layers 111, 112 in-between the input layer 110 and the output layer 113. In general, the number of hidden layers 111, 112 can be chosen arbitrarily. The number of nodes 120, . . . , 122 within the input layer 110 usually relates to the number of input values of the neural network, and the number of nodes 131, 132 within the output layer 113 usually relates to the number of output values of the neural network.

In particular, a (real) number can be assigned as a value to every node 120, . . . , 132 of the neural network 100. Here, $x(n)i$ denotes the value of the i-th node 120, . . . , 132 of the n-th layer 110, . . . , 113. The values of the nodes 120, . . . , 122 of the input layer 110 are equivalent to the input values of the neural network 100, the values of the nodes 131, 132 of the output layer 113 are equivalent to the output value of the neural network 100. Furthermore, each edge 140, . . . , 142 can comprise a weight being a real number, in particular, the weight is a real number within the interval $[-1, 1]$ or within the interval $[0, 1]$. Here, $w(m,n)i,j$ denotes the weight of the edge between the i-th node 120, . . . , 132 of the m-th layer 110, . . . , 113 and the j-th node 120, . . . , 132 of the n-th layer 110, . . . , 113. Furthermore, the abbreviation $w(n)i,j$ is defined for the weight $w(n,n+1)i,j$.

In particular, to calculate the output values of the neural network 100, the input values are propagated through the neural network. In particular, the values of the nodes 120, . . . , 132 of the (n+1)-th layer 110, . . . , 113 can be calculated based on the values of the nodes 120, . . . , 132 of the n-th layer 110, . . . , 113 by $$x_j^{(n+1)} = f\left(\sum_i x_i^{(n)} \cdot w_{i,j}^{(n)}\right).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 110 are given by the input of the neural network 100, wherein values of the first hidden layer 111 can be calculated based on the values of the input layer 110 of the neural network, wherein values of the second hidden layer 112 can be calculated based in the values of the first hidden layer 111, etc.

In order to set the values w(m,n)i,j for the edges, the neural network 100 has to be trained using training data. In particular, training data comprises training input data and training output data (denoted as ti). For a training step, the neural network 100 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 100 (backpropagation algorithm). In particular, the weights are changed according to $$w'_{i,j}{}^{(n)} = w_{i,j}{}^{(n)} - \gamma \cdot \delta_j{}^{(n)} \cdot x_i{}^{(n)}$$

wherein $\gamma$ is a learning rate, and the numbers $\delta(n)j$ can be recursively calculated as $$\delta_j^{(n)} = \left( \sum_k \delta_k^{(n+1)} \cdot w_{j,k}^{(n+1)} \right) \cdot f'\left( \sum_i x_i^{(n)} \cdot w_{i,j}^{(n)} \right)$$

based on $\delta(n+1)j$, if the (n+1)-th layer is not the output layer, and $$\delta_j^{(n)} = \left( x_k^{(n+1)} - t_j^{(n+1)} \right) \cdot f'\left( \sum_i x_i^{(n)} \cdot w_{i,j}^{(n)} \right)$$

if the (n+1)-th layer is the output layer 113, wherein f' is the first derivative of the activation function, and y(n+1)j is the comparison training value for the j-th node of the output layer 113.

Figure 4:
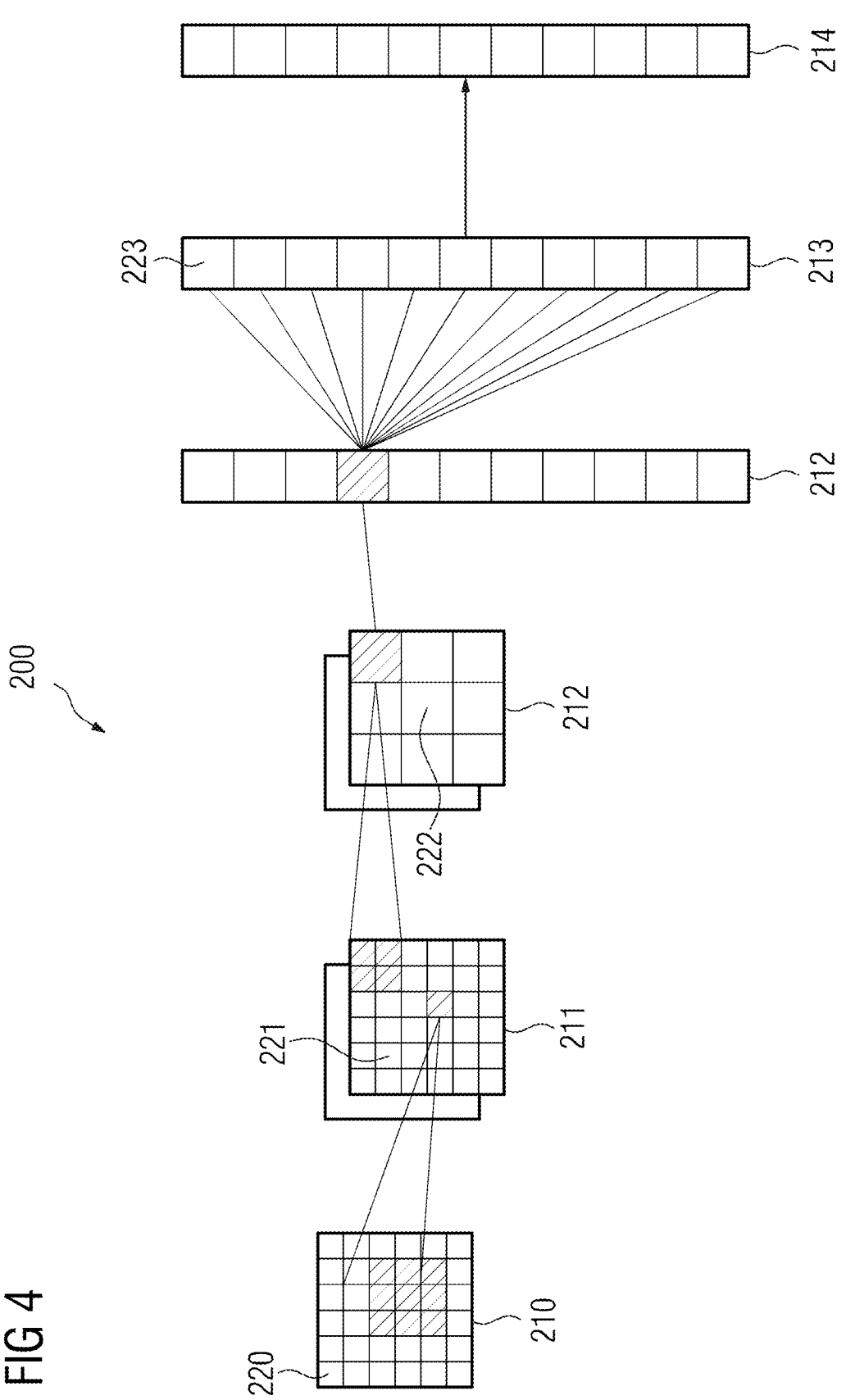
FIG. 4 a schematic representation of a convolutional neural network according to embodiments of the present invention.

FIG. 4 displays an embodiment of a convolutional neural network 200. In the displayed embodiment, the convolutional neural network comprises 200 an input layer 210, a convolutional layer 211, a pooling layer 212, a fully connected layer 213 and an output layer 214. Alternatively, the convolutional neural network 200 can comprise several convolutional layers 211, several pooling layers 212 and several fully connected layers 213, as well as other types of layers. The order of the layers can be chosen arbitrarily, usually fully connected layers 213 are used as the last layers before the output layer 214.

In particular, within a convolutional neural network 200 the nodes 220, . . . , 224 of one layer 210, . . . , 214 can be considered to be arranged as a d-dimensional matrix or as a d-dimensional image. In particular, in the two-dimensional case the value of the node 220, . . . , 224 indexed with i and j in the n-th layer 210, . . . , 214 can be denoted as x(n)[i,j]. However, the arrangement of the nodes 220, . . . , 224 of one layer 210, . . . , 214 does not have an effect on the calculations executed within the convolutional neural network 200 as such, since these are given solely by the structure and the weights of the edges.

In particular, a convolutional layer 211 is characterized by the structure and the weights of the incoming edges forming a convolution operation based on a certain number of kernels. In particular, the structure and the weights of the incoming edges are chosen such that the values x(n)k of the nodes 221 of the convolutional layer 211 are calculated as a convolution x(n)k=Kk*x(n−1) based on the values x(n−1) of the nodes 220 of the preceding layer 210, where the convolution * is defined in the two-dimensional case as $$x_k^{(n)}[i, j] = \left( K_k * x^{(n-1)} \right)[i, j] = \sum_{i'} \sum_{j'} K_k[i', j'] \cdot x^{(n-1)}[i - i', j - j'].$$

Here the k-th kernel Kk is a d-dimensional matrix (in this embodiment a two-dimensional matrix), which is usually small compared to the number of nodes 220, . . . , 224 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 220, . . . , 224 in the respective layer 210, . . . , 214. In particular, for a convolutional layer 211 the number of nodes 221 in the convolutional layer is equivalent to the number of nodes 220 in the preceding layer 210 multiplied with the number of kernels.

If the nodes 220 of the preceding layer 210 are arranged as a d-dimensional matrix, using a plurality of kernels can be interpreted as adding a further dimension (denoted as "depth" dimension), so that the nodes 221 of the convolutional layer 221 are arranged as a (d+1)-dimensional matrix. If the nodes 220 of the preceding layer 210 are already arranged as a (d+1)-dimensional matrix comprising a depth dimension, using a plurality of kernels can be interpreted as expanding along the depth dimension, so that the nodes 221 of the convolutional layer 221 are arranged also as a (d+1)-dimensional matrix, wherein the size of the (d+1)-dimensional matrix with respect to the depth dimension is by a factor of the number of kernels larger than in the preceding layer 210.

The advantage of using convolutional layers 211 is that spatially local correlation of the input data can exploited by enforcing a local connectivity pattern between nodes of adjacent layers, in particular by each node being connected to only a small region of the nodes of the preceding layer.

In the displayed embodiment, the input layer 210 comprises 36 nodes 220, arranged as a two-dimensional 6×6 matrix. The convolutional layer 211 comprises 72 nodes 221, arranged as two two-dimensional 6×6 matrices, each of the two matrices being the result of a convolution of the values of the input layer with a kernel. Equivalently, the nodes 221 of the convolutional layer 211 can be interpreted as arranges as a three-dimensional 6×6×2 matrix, wherein the last dimension is the depth dimension.

A pooling layer 212 can be characterized by the structure and the weights of the incoming edges and the activation function of its nodes 222 forming a pooling operation based on a non-linear pooling function f. For example, in the two dimensional case the values x(n) of the nodes 222 of the pooling layer 212 can be calculated based on the values x(n−1) of the nodes 221 of the preceding layer 211 as $$x^{(n)}[i,j] = f(x^{(n-1)}[id_1, jd_2], \ldots, x^{(n-1)}[id_1 + d_1 - 1, jd_2 + d_2 - 1])$$

In other words, by using a pooling layer 212 the number of nodes 221, 222 can be reduced, by replacing a number d1·d2 of neighboring nodes 221 in the preceding layer 211 with a single node 222 being calculated as a function of the values of said number of neighboring nodes in the pooling layer. In particular, the pooling function f can be the max-function, the average or the L2-Norm. In particular, for a pooling layer 212 the weights of the incoming edges are fixed and are not modified by training.

The advantage of using a pooling layer 212 is that the number of nodes 221, 222 and the number of parameters is reduced. This leads to the amount of computation in the network being reduced and to a control of overfitting.

In the displayed embodiment, the pooling layer 212 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 213 can be characterized by the fact that a majority, in particular, all edges between nodes 222 of the previous layer 212 and the nodes 223 of the fully-connected layer 213 are present, and wherein the weight of each of the edges can be adjusted individually.

In this embodiment, the nodes 222 of the preceding layer 212 of the fully-connected layer 213 are displayed both as two-dimensional matrices, and additionally as non-related nodes (indicated as a line of nodes, wherein the number of nodes was reduced for a better presentability). In this embodiment, the number of nodes 223 in the fully connected layer 213 is equal to the number of nodes 222 in the preceding layer 212. Alternatively, the number of nodes 222, 223 can differ.

Furthermore, in this embodiment the values of the nodes 224 of the output layer 214 are determined by applying the Softmax function onto the values of the nodes 223 of the preceding layer 213. By applying the Softmax function, the sum of the values of all nodes 224 of the output layer is 1, and all values of all nodes 224 of the output layer are real numbers between 0 and 1. In particular, if using the convolutional neural network 200 for categorizing input data, the values of the output layer can be interpreted as the probability of the input data falling into one of the different categories.

A convolutional neural network 200 can also comprise a ReLU (acronym for "rectified linear units") layer. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer. Examples for rectifying functions are $f(x)=\max(0,x)$, the tangent hyperbolics function or the sigmoid function.

In particular, convolutional neural networks 200 can be trained based on the backpropagation algorithm. For preventing overfitting, methods of regularization can be used, e.g. dropout of nodes 220, . . . , 224, stochastic pooling, use of artificial data, weight decay based on the L1 or the L2 norm, or max norm constraints.

Figure 5:
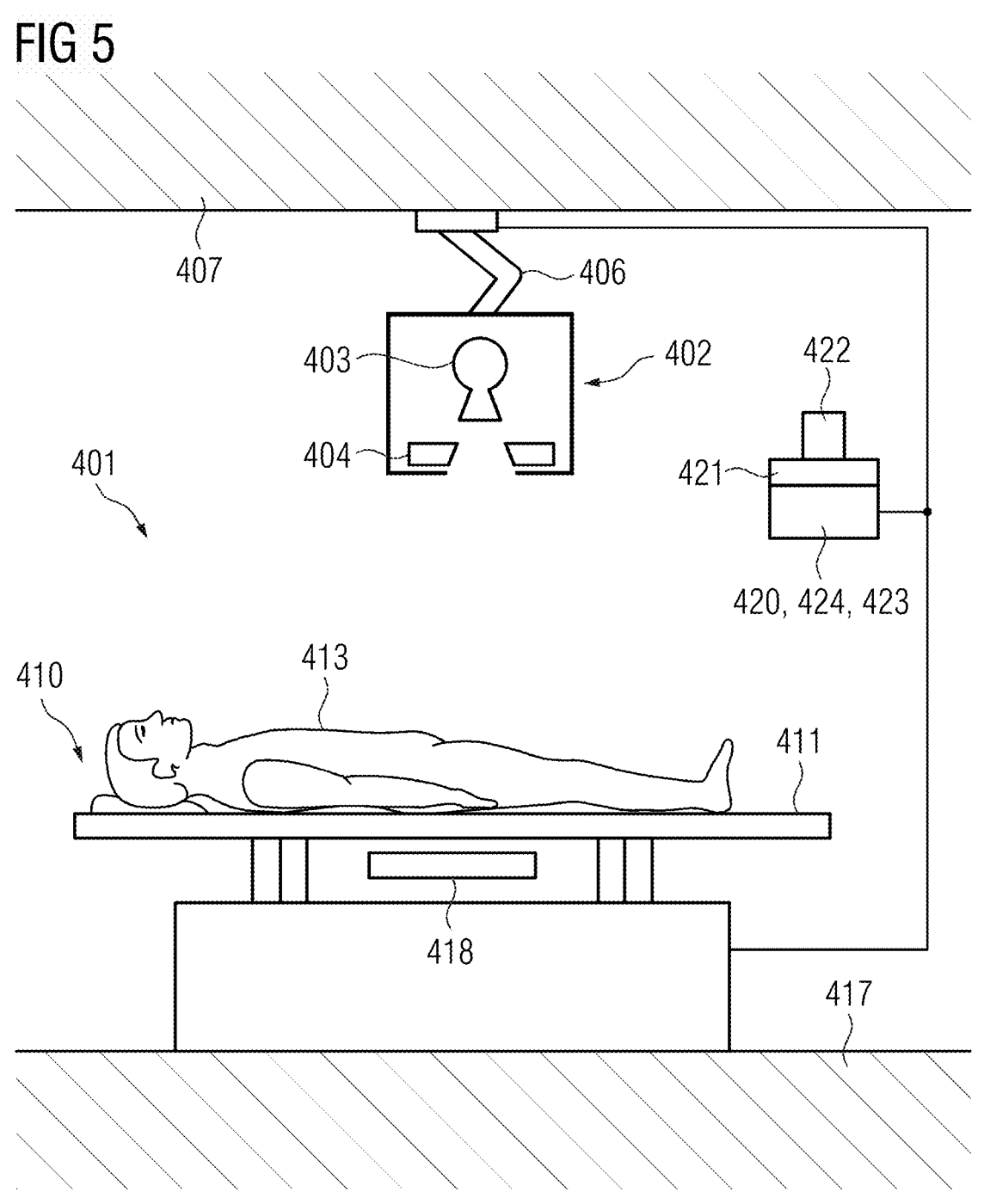

FIG. 5 shows an exemplary embodiment of a medical imaging system. As example, an X-ray system 401 according to embodiments of the present invention is shown, especially a radiography system. The X-ray system 401 has a patient positioning device 410 with a table 411 fixed to the floor 417. The object 413 lies on the table 411. The patient positioning device 410 further comprises an X-ray detector unit 418.

The X-ray system 401 comprises an X-ray source 403 and an X-ray detector unit 418. The X-ray source unit 402, which comprises the X-ray source 403 and a collimator unit 404. The X-ray source unit 402 can be connected to the ceiling 407 of the examination room by a ceiling mount 406. Via the ceiling mount 406, the X-ray source 403 can be moved.

The X-ray system 401 may also comprise an input unit 421 and an output unit 422. The input unit 421 and the output unit 422 may be connected to the control unit 420. The control unit 420 comprises the providing system 423. The control unit 420 may further comprise or be connected to the training unit 424.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been further illustrated in detail by the preferred embodiments, the present invention is not limited by the disclosed examples and other variations may be derived therefrom by those skilled in the art without departing from the scope of protection of the present invention.

What is claimed is:

1. A computer-implemented method for providing a de-identified medical image, the computer-implemented method comprising:
receiving input data, wherein the input data includes a medical image and an in-image annotation based on the medical image;
applying a first function to the input data, wherein a relevance value of pixels in the medical image is determined based on the in-image annotation, and a relevance map is generated;
applying a second function to the medical image to generate a de-identified medical image based on the relevance map;
applying a trained function to the medical image and the de-identified medical image to determine a first property in the medical image and to determine a second property in the de-identified medical image;
applying a comparison function to the first property and the second property, wherein the first property and the second property are compared to each other and a similarity value is determined, wherein
in response to the similarity value being below a similarity threshold, the relevance map is adjusted and the applying of the second function, the applying of the trained function and the applying of the comparison function are repeated; and
providing the de-identified medical image and the in-image annotation.
2. The computer-implemented method according to claim 1, wherein the applying of the second function comprises: modifying, blurring, adding noise or adding geometrical distortions in regions with pixels of lower relevance.

3. The computer-implemented method according to claim 2, wherein a strength of the modifying, blurring, adding noise or adding geometrical distortions depends on relevance values of the pixels.

4. The computer-implemented method according to claim 3, wherein the relevance map comprises relevance values ranging from 0 to 1.

5. The computer-implemented method according to claim 3, wherein the relevance value is determined based on a distance map, the distance map being based on the in-image annotation and pixels inside the in-image annotation.

6. The computer-implemented method according to claim 5, wherein another trained function is applied to the medical image, wherein additional non-relevant pixels are determined based on information in the medical image.

7. The computer-implemented method according to claim 3, wherein at least one of the first property or the second property is determined by an object segmentation task, an object detection task, an image classification task, or a regression task.

8. The computer-implemented method according to claim 1, wherein the relevance map comprises relevance values ranging from 0 to 1.

9. The computer-implemented method according to claim 1, wherein the relevance value is determined based on a distance map, the distance map being based on the in-image annotation and pixels inside the in-image annotation.

10. The computer-implemented method according to claim 1, wherein another trained function is applied to the medical image, wherein additional non-relevant pixels are determined based on information in the medical image.

11. The computer-implemented method according to claim 1, wherein at least one of the first property or the second property is determined by an object segmentation task, an object detection task, an image classification task, or a regression task.

12. The computer-implemented method according to claim 1, wherein the similarity value is a Hausdorff distance, a difference of normalized probabilities or a difference of prediction results.

13. The computer-implemented method according to claim 1, wherein the medical image is an X-ray image.

14. A non-transitory computer program product comprising instructions which, when executed by a providing system, cause the providing system to perform the method of claim 1.

15. A non-transitory computer-readable medium comprising instructions which, when executed by a providing system, cause the providing system to perform the method of claim 1.

16. A providing system comprising:
a memory storing computer-executable instructions; and
at least one processor configured to execute the computer-executable instructions to cause the providing system to perform the method of claim 1.

17. A providing system comprising:
a first interface configured to receive input data, wherein the input data includes a medical image and an in-image annotation based on the medical image;
a first computation unit configured to apply a first function to the input data, wherein a relevance value of pixels in the medical image is determined based on the in-image annotation, and a relevance map is generated;
a second computation unit configured to apply a second function to the medical image to generate a de-identified medical image based on the relevance map;
a third computation unit configured to apply a trained function to the medical image and the de-identified medical image to determine a first property in the medical image and a second property in the de-identified medical image;
a fourth computation unit configured to apply a comparison function to the first property and the second property, wherein the first property and the second property are compared to each other and a similarity value is determined, wherein
in response to the similarity value being below a similarity threshold, the relevance map is adjusted, and the second function, the trained function and the comparison function are reapplied; and
a second interface configured to provide the de-identified medical image and the in-image annotation.

18. A medical imaging system comprising the providing system according to claim 17.

* * * * *